United States Patent [19]

Harnik et al.

[11] Patent Number: 4,659,704
[45] Date of Patent: Apr. 21, 1987

[54] 19-HYDROXYALDOSTERONE AND ITS PREPARATION

[75] Inventors: Marcel Harnik; Yoel Kashman, both of Tel Aviv, Israel

[73] Assignee: Ramot University Authority for Applied Research & Industrial Development Ltd., Tel Aviv, Israel

[21] Appl. No.: 736,548

[22] Filed: May 21, 1985

[51] Int. Cl.⁴ ............................................. A61K 31/58
[52] U.S. Cl. ..................................... 514/172; 540/24; 540/74; 540/91; 540/92
[58] Field of Search ................. 260/239.55 R; 514/172

[56] References Cited

U.S. PATENT DOCUMENTS 4,309,423 1/1982 Biollaz ........................ 260/239.55 R Primary Examiner—Elbert L. Roberts
Attorney, Agent, or Firm—Stiefel, Gross, Kurland & Pavane

[57] ABSTRACT

There is provided the novel compound 19-hydroxyaldosterone. There is provided a process for its preparation. There are further provided pharmaceutical compositions comprising this compound as active ingredient. These are useful, amongst others, as mineralocorticoid drugs and as drug against Addison's disease.

5 Claims, 2 Drawing Figures

19-HYDROXYALDOSTERONE AND ITS PREPARATION

FIELD OF THE INVENTION

A novel steroid compound, 19-hydroxyaldosterone has been prepared. This compound exhibits full mineralocorticosteroid activity in the Kagawa bioassay.

The invention relates to functional derivatives of the above compound and a process for the preparation thereof.

It also relates to pharmaceutical compositions containing such compounds as active ingredients. The compounds are of value, amongst others, in the treatment of Addison's disease.

BACKGROUND OF THE INVENTION

Steroids, such as 11-deoxycorticosterone and androstenedione, having an hydroxy substituent at the 19-position, have been described recently and have been shown to be of interest. 19-Hydroxy-11-deoxycorticosterone was detected in regenerating rat adrenal incubations, and it was also detected as a product of 11-deoxycorticosterone metabolism by rat adrenal. It was further discovered that 19-hydroxyandrostenedione is a potent hypertensinogenic steroid in humans.

SUMMARY OF THE INVENTION

The invention relates to the novel compound 19-hydroxyaldosterone and to functional derivatives thereof. It further relates to a process for the production of these compounds.

It further relates to pharmaceutical compositions containing same as active ingredient.

The novel compounds are of value in human medicine. They exhibit mineralocorticoid activity causing sodium retention and raising blood pressure. The compounds of the invention are of value in the treatment of Addison's disease. They are also of value in the study of the etiology of hypertension. Preliminary studies indicate that the compound 19-hydroxyaldosterone causes anti-natriuresis and kaliuresis at a dose of about 25 micrograms per rat. In short-circuit current measurements it was shown that the compounds showed mineralocorticoid activity approaching that of aldosterone. The compound exists as a mixture of mainly two isomers, and the invention relates to the isomeric mixture as well as to each of the individual isomers.

The pharmaceutical compositions of the invention comprise the active ingredients in combination with a suitable conventional adjuvant or carrier. The 19-hydroxyaldosterone was prepared by a sequence of process steps as set out in the enclosed reaction schemes. It is clear that this reaction scheme can be modified at will.

BRIEF DESCRIPTION OF THE DRAWINGS

The novel compound 19-hydroxyaldosterone is prepared, in accordance with the present invention, by the process illustrated in the accompanying drawings, in which.

Figure 1:
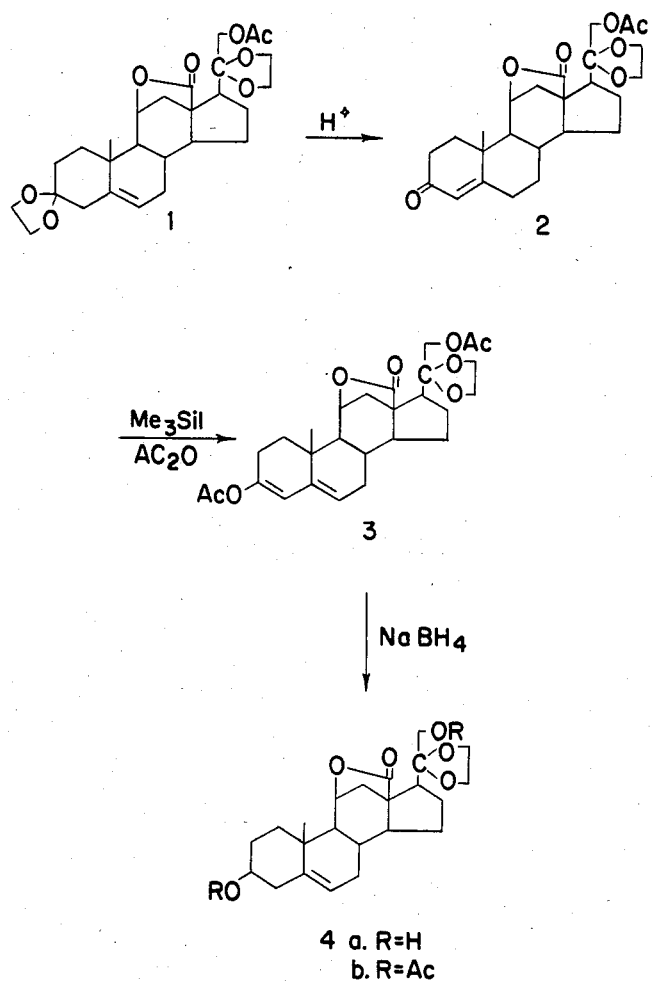
FIG. 1 is a flow sheet illustrating the conversion of the raw material, 21-acetoxy-5-pregnene-3,20-dione-di-(ethylene ketal)-18,11β-lactone (1), to the intermediate 3β,21-dihydroxy-5-pregnen-20-one-20-ethylene ketal-18,11β-lactone (4a), or the 3,21-diacetate (4b) thereof.
Figure 2:
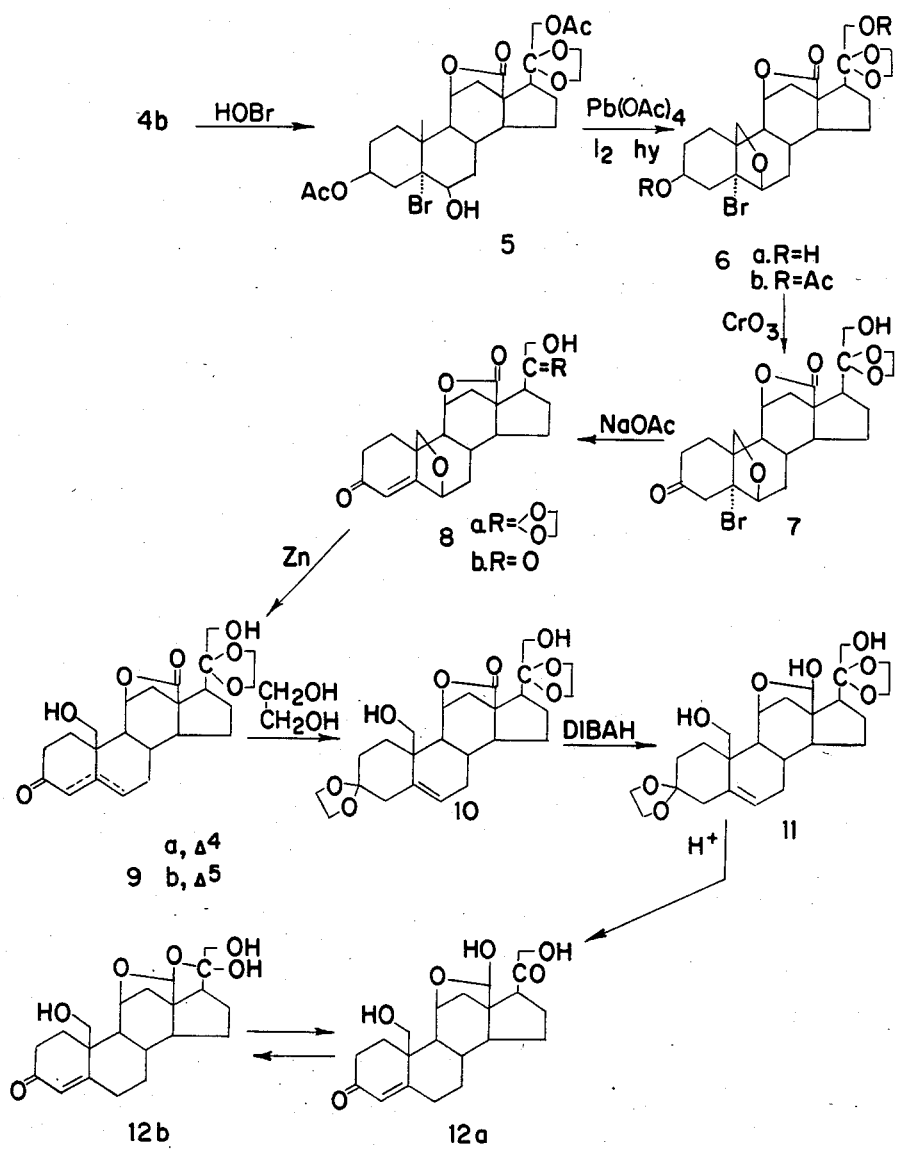
FIG. 2 is a flow sheet showing the conversion of the diacetate to the desired 19-hydroxyaldosterone product 12(a,b).

Thus, according to a preferred embodiment of the invention the reaction comprises the following steps:

The starting material was 21-acetoxy-4-pregnene-3,20-dione-20-ethylene ketal-18,11β-lactone in which the double bond was moved from the 4,5- to the 5,6-position by enol acetylation to 3,21-diacetoxy-3,5-pregnadien-20-one-20-ethylene ketal-18,11β-lactone, followed by borohydride reduction and acetylation by conventional means, giving 3,21-diacetoxy-5-pregnen-20-one-20-ethylene ketal-18,11β-lactone which was converted to the corresponding 6β,19-oxido compound by addition of hypobromous acid followed by the hypoiodite reaction of the bromohydrin, followed by mild saponification to yield the corresponding diol, 5-bromo-6β,19-epoxy-3β,21-dihydroxy-5α-pregnan-20-one-20-ethylene ketal-18,11β-lactone, followed by selective oxidation to the corresponding 3-one, which was dehydrobromiated to 6β,19-epoxy-21-hydroxy-4-pregnene-3,20-dione-20ethylene ketal-18,11β-lactone, subjecting same to reductive ring opening to provide a mixture of 19,21-dihydroxy-4-pregnene-3,20-dione-20-ethylene ketal-18,11β-lactone and the corresponding 5-ene isomer, converting the above mixture to the 3,20-diketal and subjecting same to reduction with diisobutyl aluminum hydride to the hemiacetal 11β,18-epoxy-18,19,21-trihydroxy-5-pregnene-3,20-dione-3,20-di-(ethylene ketal), which was hydrolyzed to the desired 19-hydroxyaldosterone.

This compound can be easily converted by conventional processes to a variety of 18,19- and 21-mono, di- and triesters in the formula

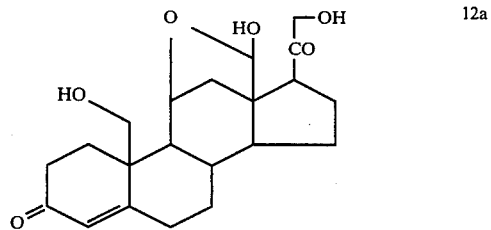

and 19- and 21-mono and diesters in the isomeric compound of formula

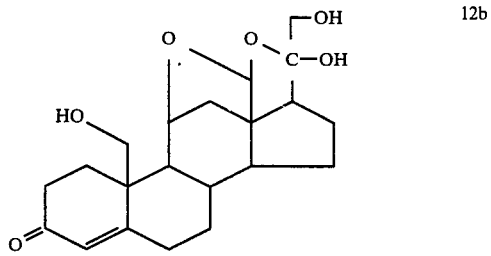

EXPERIMENTAL

Merck A.G. silica gel ("60", mesh 70–230) was used in column chromatography. TLC was performed with acetone-hexane or $CHCl_3$-ethanol mixtures and the plates (silica gel Merck F254) were sprayed with 10% $H_2SO_4$ in ethanol before heating. $^1$H-NMR spectra (in $CDCl_3$ with TMS as internal standard) were obtained

21-Acetoxy-4-pregnene-3,20-dione-20-ethylene ketal-18,11β-lactone (2)

A solution of 19.3 g of 21-acetoxy-5-pregnene-3,20-dione-di-(ethylene ketal)-18,11β-lactone (1) in 300 ml of dioxane was treated with 7 ml of 0.5N HCl and allowed to stand at 20° C. for 3 days with occasional TLC monitoring (acetone-hexane 1:2). Addition of 500 ml of water and 100 ml of saturated aq. $NaHCO_3$ was followed by three extractions with MDC, drying of the extracts with $Na_2SO_4$ and evaporation in vacuo at 40° C. The gum was chromatographed on 800 g of silica gel using PE-acetone 4:1 containing a trace of $Et_3N$, collecting 250 ml fractions. Flasks 25–38 gave 3.8 g of starting diketal 1, while fractions 54–84 furnished 10.6 g of the desired 3-one 2, m.p. 155°–160° C. (reported 160°–2° C.). Elution with a 1:1 solvent mixture yielded varying amounts of 21-hydroxy-4-pregnene-3,20-dione-18,11β-lactone.

3,21-Diacetoxy-3,5-pregnadien-20-one-20-ethylene ketal-18,11β-lactone (3) and

3β,21-dihydroxy-5-pregnen-20-one-20-ethylene ketal-18,11β-lactone (4a)

An ice-cold solution of 4.3 g of 2 in 50 ml of acetic anhydride was treated with 5 ml of trimethylchlorosilane followed by 7.5 g of NaI (weighed out under $N_2$) and swirled with occasional ice-cooling, with precipitation of NaCl. The mixture was kept in the dark at room temperature for 1 h, then poured in a thin stream into a mechanically stirred suspension of 250 g of ice in 150 ml of aq. saturated $NaHCO_3$ solution and 200 ml of MDC. Ten ml of 5% sodium bisulfite solution was added, the aqueous phase was reextracted with 2×150 ml portions of MDC, and the combined extracts were treated with 1 ml of pyridine and dried with $Na_2SO_4$. The solvents were removed in vacuo, finally with the aid of an oil pump at 55° C. (bath temperature). The residual oil was treated with 2 drops of pyridine and 20 g of ice to decompose any residual acetic anhydride and initiate crystallization of the enol acetate 3, exhibiting $\lambda^{KBr}_{max}$ 5.66 and 5.74 (sh) μ. It was washed with water by decantation, directly treated with 130 ml of ethanol and 6.7 g of sodium borohydride, and the suspension was refluxed for 30 min. Most of ethanol was then removed on the steam bath with a stream of $N_2$ and 200 ml of water was added. The clear solution was heated for an additional 30 min, cooled in ice, poured into a 1 L separatory funnel containing 400 ml of MDC, acidified with 15 ml of acetic acid, and the lactone was extracted with a total of 700 ml of MDC. The combined extracts were washed with aq. $NaHCO_3$, dried with $Na_2SO_4$ and evaporated in vacuo. The residue was treated with a little ether, the diol 4a collected and washed with ether: 3.37 g, m.p. 206°–212° C. The pure sample had m.p. 214°–6° C. (acetone with a trace of $Et_3N$); $\lambda^{KBr}_{max}$ 2.96 and 5.66μ; δ 1.123 (s, 19-$CH_3$), 2.93 (dd, J=11.6, 12-H), 3.41 (m, 3α-H), 3.46, 3.54 (ABq, J=7, 21-$H_2$), 3.98 (m, 20-dioxolane), 4.73 (d, J=6, 11α-H) and 5.28 (brd, J=3.5, 6-H) ppm; EI: m/z 386 ($M^+$—$H_2O$; 5%), 374 ($M^+$—CHOH; 100)(usual fragmentation in 21-ol-20-dioxolanes), 356 ($M^+$—OHOH—$H_2O$; 16), 312 ($M^+$—CHOH—$CO_2$; 9) and

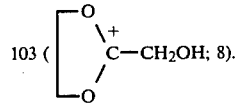

103 ($\begin{bmatrix} -O \\ \phantom{x} \\ -O \end{bmatrix} \overset{+}{\underset{\phantom{x}}{C}}$—$CH_2OH$; 8).

The 3,21-diacetate 4b, prepared in the usual manner with acetic anhydride and pyridine, had m.p. 161°–4° C. (ether-PE); $\lambda^{KBr}_{max}$ 5.68 and 5.76μ; δ 1.136 (s, 19-$CH_3$), 2.034, 2.082 (s,s, 3-OAc, 21-OAc), 2.98 (dd, J=11;6, 12-H), 3.97 (m, 20-dioxolane), 3.97, 4.08 (d,d, ABq, J=12, 21-$H_2$), 4.59 (m, 3α-H), 4.74 (d, J=6, 11α-H) and 5.39 (brd, J=3.5, 6-H) ppm; EI: m/z 416 ($M^+$—HCOAc; 100%), 356 ($M^+$—CHOAc—AcOH; 93), 312 ($M^+$—CHOAc—AcOH—$CO_2$; 16) and

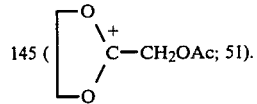

145 ($\begin{bmatrix} -O \\ \phantom{x} \\ -O \end{bmatrix} \overset{+}{\underset{\phantom{x}}{C}}$—$CH_2OAc$; 51).

3β,21-Diacetoxy-B 5-bromo-6β-hydroxy-5α-pregnan-20-one-20-ethylene ketal-18,11β-lactone (5)

An ice-cooled solution of 3.0 g of 4b in 60 ml of dioxane was treated with 7.6 ml of 4.6% aq. perchloric acid, followed in portions over a 5 min period by 3.3 g of N-bromoacetamide. After 30 min at room temperature in the dark the solution was shaken with a mixture of 150 ml of saturated aq. $NaHCO_3$, 100 ml of water, 40 ml of 5% aq. sodium metabisulfite solution and 200 ml of MDC, and then reextracted with 2×50 ml portions of MDC. The combined extracts were dried with $Na_2SO_4$ and evaporated in vacuo to an oil containing 5, which was best directly converted to 6b without further purification. A 100 mg sample was chromatographed on 10 g of silica gel: elution with PE-acetone 4:1 gave at first a trace of the starting 4b followed by the bromohydrin 5, 41 mg, m.p. 156°–160° C. (dec.) The pure sample had m.p. 166°–167° C. (methanol); $\lambda^{KBr}_{max}$ 2.91, 5.65, 5.72 and 5.85μ; δ 1.415 (s, 19-$CH_3$), 2.033, 2.079 (s,s, 3-OAc, 21-OAc), 2.921 (dd, J=11.3;6.3, 12-H), 3.99 (m, 20-dioxolane), 3.99 (m, 21-H), 4.093 (d, J=11.8, 21-H), 4.188 (brs, 6α-H), 4.67 (d, J=6.2, 11α-H) and 5.45 (m, 3α-H) ppm.

3β,21-Diacetoxy-5-bromo-6β,19-epoxy-5α-pregnan-20-one-20-ethylene ketal-18,11β-lactone (6b)

A suspension of 20 g of lead tetraacetate (washed with acetic acid, pressed and weighed moist) and 10 g of $CaCO_3$ in 600 ml of cyclohexane was refluxed with stirring for 30 min. Five and three tenths g of $I_2$ was added, followed by the crude bromohydrin 5 (prepared the same day from 3.0 g of 4b) dissolved in 25 ml of MDC. The mixture was refluxed with stirring and illumination with a 150 W spotlight bulb until the purple color disappeared: in 8 runs the time varied from 18 to 30 min without affecting the yield. The mixture was cooled briefly in ice, while hot filtered with suction, the precipitate was washed with a total of 100 ml of MDC and the combined filtrates were shaken for a few seconds with 400 ml of 2.5% aqueous sodium thiosulfate. The aq. layer was quickly separated before a voluminous lead salt started to precipitate, and the organic phase was washed with additional 200 ml of thiosulfate solution. The combined aqueous solutions were backwashed with 50 ml of MDC, and the combined organic phases were washed with 100 ml of saturated aq. NaHCO$_3$, dried with Na$_2$SO$_4$ and distilled in vacuo to a volume of about 100 ml. Precipitation was completed by addition of 70 ml of PE and ice-cooling. The crude 6b was collected and washed with PE, 3.6–3.9 g (a small additional amount could be obtained by chromatography of the filtrate). For purification, 13.5 g of the solid, absorbed on 60 g of silica gel, was chromatographed on a column of 700 g of silica gel. Elution with PE-acetone 4:1 containing a trace of Et$_3$N gave in fractions 32–44 (250 ml each) a total of 6.5 g of pure 6b, m.p. 142°–5° C. Rechromatography of the borderline fractions furnished additional 0.7 g; $\gamma^{KBr}_{max}$ 5.63, 5.72 and 5.76μ; δ 2.039, 2.080 (s,s, 3-OAc, 21-OAc), 2.89 (dd, J=11.6, 12-H), 3.97 (m, 21-H), 4.087 (d, J=11.7, 21-H'), 3.97 (m, 20-dioxolane), 3.99, 4.04 (d,d, J=9;9, 19-H$_2$), 4.08 (brs, 6α-H) and 5.18 (m, 3α-H) ppm.

5-Bromo-6β,19-epoxy-3β,21-dihydroxy-5α-pregnan-20-one-20-ethylene ketal-18,11β-lactone (6a)

A solution of 4.0 g of the diacetate 6b in 120 ml of hot methanol was treated with a solution of 3.2 g of KHCO$_3$ in 40 ml of water, refluxed for 1 h and concentrated in vacuo at 35° C. to a low volume. Water (100 ml) and acetic acid (4 ml) were added and the mixture was extracted with a total of 350 ml of MDC. The combined extracts were washed with aq. NaHCO$_3$, dried with Na$_2$SO$_4$, filtered and divided into two halves, each of which was distilled in vacuo at 40° C. until the diol 6a was obtained as a foam free of methanol.

6β,19-Epoxy-21-hydroxy-4-pregnene-3,20-dione-20-ethylene ketal-18,11β-lactone (8a)

Each portion of 6a (vide supra) was dissolved in 300 ml of hot acetone in a 1 L round bottom flask, cooled in an ice-bath with swirling for 5 min and treated with 3 ml of the Jones reagent. After swirling in ice for additional 5 min 3 ml of isopropanol was added, followed by 5 g of NaHCO$_3$ and 80 ml of water. The mixture was distilled in vacuo to remove most of the acetone until a volume of about 70 ml was reached, and then cooled in ice while the second half of 6a was processed in a similar manner. Both batches were combined and filtered through a large sintered glass funnel. The sucked-dry green precipiate was washed with a total of 150 ml of MDC, the aqueous phase was extracted with a total of 200 ml of MDC, the combined extracts were dried with Na$_2$SO$_4$ and evaporated in vacuo. The residual gum (2.7–2.9 g) containing 5-bromo-6β,19-epoxy-21-hydroxy-5α-pregnane-3,20-dione-20-ethylene ketal-18,11β-lactone (7) was refluxed in 100 ml of ethanol containing 5 g of sodium acetate for 1 h, the solvent was evaporated to dryness at 40° C. and the residue worked up with water and MDC. The dried extracts were evaporated to furnish 2.3–2.7 g of a crude gum which was chromatographed on 270 g of silica gel using CHCl$_3$-ethanol 98:2 containing a trace of Et$_3$N. Concentration of the early fractions yielded the desired ketal 8a which was collected with the aid of PE and washed with EtOAc: 1.23 g, m.p. 188°–190° C.; $\lambda^{KBr}_{max}$ 2.96, 5.60 and 5.99μ; δ 2.987 (dd, J=11.5;6.2, 12-H), 3.995 (m, 20-dioxolane), 3.499 (ABq, J=11.4, 21-H$_2$), 3.50, 4.485 (d,d, J=8.4, 19-H$_2$), 4.715 (d, J=4.7, 6α-H), 4.776 (d, J=6.1, 11α-H) and 5.868 (s, 4-H) ppm. On acetylation the AB system appears at 3.97 and B 4.10 (d,d, J=11;11, 21-H$_2$) ppm; EI: m/z 372 (M$^+$—CO$_2$; 5%), 341 (M$^+$—CO$_2$—CH$_2$OH; 18),

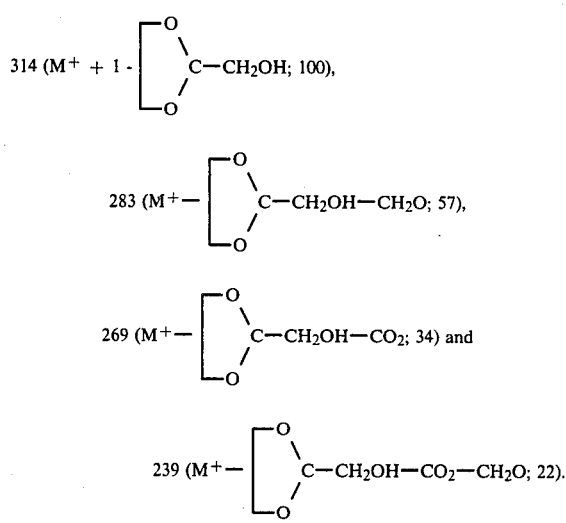

Continued elution furnished 220 mg of 6β,19-epoxy-21-hydroxy-4-pregnene-3,20-dione-18,11β-lactone (8b) which, after crystallization from acetone, had m.p. 229°–231° C. (dec.); $\lambda^{KBr}_{max}$ 2.90, 5.66, 5.85 and 5.97μ; δ 3.16 (dd, J=11;6, 12-H$_2$), 3.52, 4.47 (ABq, J=8.2, 19-H$_2$), 4.235 (d, J=18.4, 21-H), 4.48 (d, J=18.2, 21-H'), 4.730 (d, J=4, 6α-H), 4.907 (d, J=6.2, 11α-H) and 5.883 (s, 4-H) ppm.

The 20-one 8b (42 mg) could also be obtained by hydrolysis of 8a (80 mg) in dioxane (3 ml) containing 5% HCl (0.5 ml) at room temperature for 48 h, followed by the usual workup.

19,21-Dihydroxy-4-pregnen-3,20-dione-20-ethylene ketal-18,11β-lactone (9a)

A solution of 300 mg of the oxidolactone 8a in 20 ml of acetic acid was diluted with 2 ml of water and, with mechanical stirring, treated on the steam bath over a 6 min period with 7 g of zinc powder. The mixture was cooled in ice to room temperature, filtered with suction, the zinc washed with 3×5 ml portions of acetic acid, the combined filtrates were distilled in vacuo at 38° C. and the residual semisolid was worked up with water and MDC. The combined MDC extracts were washed with aq. NaHCO$_3$, dried, evaporated in vacuo and the residue was crystallized from acetone to furnish 72 mg of 9a, m.p. 225°–7° C.; $\lambda^{KBr}_{max}$ 2.90, 5.69 and 6.06μ; δ 3.46 (dd, J=12.0;7.7, 21-H), 3.52 (dd, J=12.0;5.3, 21-H'), 3.99 (m, 20-dioxolane), 3.63 (dd, J=12.7;9.5, 19-H), 4.08 (dd, J=12.7;6.3, 19-H'), 4.93 (d, J=6.1, 11α-H) and 5.87 (s, 4-H) ppm; EI: m/z 388 (M$^+$—CHOH; 80%), 370 (M$^+$—CHOH—H$_2$O; 7), 358 (M$^+$—2CHOH; 100) and 314 (M$^+$—2CHOH—CO$_2$; 6); CI: 419 (M$^+$+1; 31%), 401 (M$^+$+1—H$_2$O; 11) and 389 (M$^+$+1—CHOH; 100).

19,21-Dihydroxy-5-pregnene-3,20-dione-3,20-di-(ethylene ketal)-18,11β-lactone (10)

A. Reduction of 8a with zinc-acetic acid-isopropanol.

A solution of 2.35 g of 8a in 350 ml of isopropanol and 30 ml of acetic acid was refluxed with stirring for 40 min with 60 g of zinc powder (activated by washing with 5% HCl, isopropanol and air-dried). The mixture was cooled, filtered with suction and the solid washed well with isopropanol. The combined filtrates were distilled to dryness in vacuo, the residue treated with 200 ml of water and extracted with 4×100 ml portions of MDC. The extracts were washed with aq. NaHCO$_3$, dried and evaporated to a gum (2.36 g) containing a mixture of 19,21-dihydroxy-4-pregnene-3,20-dione-20-ethylene ketal-18,11β-lactone (9a) and its 5-ene isomer 9b in variable proportions.

B. Ketalization with ethylene glycol.

A mixture of 9a and 9b (2.86 g) obtained as above was treated with 200 ml of ethylene glycol and 280 mg of p-toluenesulfonic acid, and distilled in vacuo with mechanical stirring at 60°–5° C. over a 3.5 h period until a volume of about 50 m remained. The mixture was cooled, treated with 100 ml of saturated aq. NaHCO$_3$ and 20 ml of saturated NaCl solution, and extracted with 100 ml and 3×70 ml portions of MDC. The dried extracts were evaporated in vacuo and the residual semisolid was chromatographed on 250 g of silica gel using CHCl$_3$-ethanol 98:2 with a trace of Et$_3$N as the eluting agent to afford 950 mg of the diketal 10, m.p. 211°–3° C., resolidifying and melting at 228° C. (EtOAc); $\lambda^{KBr}_{max}$ 2.82 and 5.68μ; δ 2.977 (dd, J=11.5;6.6, 12-H), 3.47 (dd, J=12.0;8, 21-H), 3.50 (dd, J=11.5;6, 21-H'), 3.630 (dd, H=13;9, 19-H), 3.758 (dd, J=13;5.8, 19-H'), 3.976 (m, 3 and 20-dioxolanes), 4.971 (d, J=6.2, 11α-H) and 5.51 (brdd, J~5;1.5, 6-H) ppm; EI: m/z 462 (M+,1%), 432 (M+—CHOH; 73), 402 (M+—2CHOH; 100),

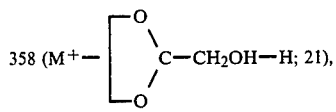
358 (M+—[O\C—CH$_2$OH—H; 21]/O),

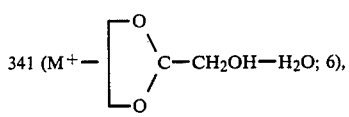
341 (M+—[O\C—CH$_2$OH—H$_2$O; 6]/O),

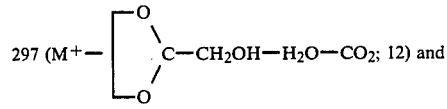
297 (M+—[O\C—CH$_2$OH—H$_2$O—CO$_2$; 12] and /O),

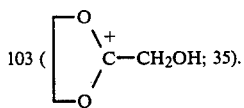
103 ([O\+C—CH$_2$OH; 35]/O).

Purification of small amounts by TLC could be simplified by adding Reichstein's Compound S and cortisol as fluorescing markers running, respectively, in front and behind 10 in CHCl$_3$-ethanol 30:2.

11β,18-Epoxy-18,19,21-trihydroxy-5-pregnene-3,20-dione-3,20-di-(ethylene ketal)

A mechanically stirred solution of 742 mg of 10 in 20 ml of dry MDC was treated in a N$_2$ atmosphere at −30° C. with 15 ml of 1M DIBAH solution in toluene from a syringe through a rubber septum. The mixture was slowly stirred at −20° C. for 1 hour, cooled to −30° C., treated again with 15 ml of DIBAH solution, stirred at −20° C. for another hour, treated at −40° C. with 50 ml of MDC, then with 20 ml of 2M isopropanol solution in toluene, and at 0° C. with 1.5 ml of water. Next 10 g of celite and 15 g of Na$_2$SO$_4$ were added, and after stirring for 15 min the mixture was filtered with suction through a large sintered glass funnel. The gelatinous precipitate was washed with 100 ml of MDC, transferred into a column (30 mm diameter) and eluted with a total of 4 L of THF, applying suction to maintain a desirable dripping rate. The filtrate and eluate were evaporated in vacuo and the oily residue chromatographed on 65 g of silica gel with CHCl$_3$-ethanol 98:2 containing a trace of Et$_3$N. The suitable fractions were pooled, the solvent was evaporated in vacuo and crystallization of 11 initiated by addition of 7 ml of EtOAc. The product was washed with more EtOAc, weighed 295 mg and had the m.p. 196°–9.5° C.; $\lambda^{KBr}_{max}$ 2.94μ; δ 3.5–3.7 (m, 21-H$_2$), 3.7–3.9 (m, 19-H$_2$), 4.0 (m, 3 and 20-dioxolanes), 4.461 (d, J=6.2, 11α-H), 4.753 (d, J=6.6, 11α-H, minor isomer), 4.597 (s, 18-H, minor isomer), 5.168 (s, 18-H), 5.49 (brd, J=3, 6-H) and 5.53 (brd, 6-H, minor isomer) ppm; EI: m/z 446 (M+—H$_2$O; 3%), 417 (M+—H$_2$O—CHO; 97), 399 (M+—2H$_2$O—CHO; 100) and 390 (M+—CH$_2$OH—CO$_2$; 18).

19-Hydroxyaldosterone 12a 12b

A solution of 51 mg of diketal 11 in 4 ml of dioxane was treated with 0.2 ml of 5% HCl and stored at 19° C. for 10 h, at which time TLC indicated the presence of mere traces of the starting material. Saturated aq. NaHCO$_3$ solution (10 ml) and MDC (50 ml) were added and the aqueous phase was reextracted with 4×15 ml portions of MDC. The dried (Na$_2$SO$_4$) extracts were evaporated in vaco at 35° C., the residue was applied to 8 TLC plates 0.2 mm thick and developed with CHCl$_3$-ethanol 30:2.5. The appropriate zone was eluted with 10 ml of methanol each and the combined solutions were evaporated in vacuo. The gum was dissolved in a little MDC, the solution was filtered through a cotton plug to remove residual silica, evaporated in a stream of N$_2$ and scratched with ether to afford 19 mg of crystalline 12, pure in TLC. The compound is moderately soluble in warm ether and very soluble in water: by washing the glassware and the cotton plug with water and evaporating in a desiccator over H$_2$SO$_4$ additional 2 mg of pure 12 was obtained. The compound melts at 110°–120° C.; $\lambda^{KBr}_{max}$ 2.93, 5.82 (w) and 6.02μ (FIG. 3); δ 4.065 (brd), 3.99 (brd, J=13, 21-H$_2$), 4.40, 4.245 (d,d, J=18;18, 21-H$_2$; this system only partially seen), 4.757 (d, J=6.3, 19-H$_2$, one isomer), 4.969 (d, J=5.6, 19-H$_2$, another isomer), 5.115 (s, 18-H, one isomer), 5.489 (s, 18-H, another isomer) and 5.827 (s, 4-H) ppm.

The key intermediate employed in the synthesis was the ketal 2 which was prepared according to Lederman et al: Anal. Biochem. 51 (1973) 193 (FIG. 1). It was obvious that the 18,11β lactone should be preserved as a relatively insensitive moiety up to the penultimate step of synthesis, that is the reduction to the hemiacetal 11.

The 5,6-double bond was then introduced, preferably by enolacetylation of 2, followed by sodium borohydride reduction.

However, attempts at conversion of 2 into 3 were met with failure due to the sensitivity of the side-chain: acetic anhydride or isopropenyl acetate with a variety of acidic catalysts led mostly to splitting off of the 20-ketal group; also acetyl chloride or acetic anhydride in warm pyridine caused extensive decomposition. On the other hand, the mild enol acetylation method employing acetic anhydride, trimethylchlorosilane and NaI at room temperature proved to be eminently suitable for the preparation of 3, which was best not purified but directly treated with sodium borohydride to afford the ketal 4a in 86% overall yield from 2.

The 3β-ol 4a was then acetylated and the diacetate 4b reacted with N-bromoacetamide and perchloric acid to furnish the bromohydrin 5, the ketal group at $C_{20}$ being stabilized by the presence of the acetate at $C_{21}$.

The bromohydrin easily lost HBr during the isolation; the crude 5 was, therefore, directly reacted with lead tetraacetate, iodine and $CaCO_3$ under illumination; chromatographic purification gave the cyclic derivative 6b in 60% overall yield from 4b.

The diacetate 6b was next saponified with boiling bicarbonate and the diol 6a selectively oxidized with the Jones reagent at $C_3$, the secondary hydroxyl having preference over the primary $C_{21}$-hydroxyl, without extensive hydrolysis of the ketal at $C_{20}$. The resulting bromoketone 7 was unstable and therefore directly dehydrobrominated with sodium acetate in ethanol: chromatography afforded the unsaturated ketone 8a in 43% overall yield from 6b, and a small amount of the 20-one 8b.

Reductive ring opening of 6,19-oxides is commonly performed with zinc and acetic acid, when partial acetylation of the 19-hydroxyl may take place. Since acetylation can be prevented by the use of aqueous acetic acid the ketal 8a was subjected to a brief treatment with zinc and 90% acetic acid, when a 23% of the desired 4-en-19-ol 9a was obtained. Zinc or amalgamated zinc in refluxing isopropanol were ineffective; however zinc in a mixture of isopropanol and acetic acid, proved to be useful in the present synthesis, allowing conversion of 8a into a mixture of 9a and its 5-ene isomer 9b, which was directly ketalized with ethylene glycol and p-toluenesulfonic acid to yield the diketal 10 in 30% overall yield from 8a.

Reduction of the lactone function in 10 to the hemiacetal 11 with DIBAH was next carried out. A large excess of the reagent was required and the product was accompanied by more polar by-products. Furthermore, the products of decomposition of DIBAH with isopropanol and water were tightly bound to the triol 11 which could be desorbed, preferably with a large volume of THF. The product was purified by chromatography and proved to be a mixture of the two $C_{18}$ epimers, as indicated in the NMR spectrum by two sets of protons at positions 6, 11α and 18.

The synthesis of 19-hydroxyaldosterone (12) was then completed by a mild hydrolysis of its diketal 11. The hydroxyl at position 19 promotes the hydrolysis of the ketal at $C_3$, the rate being faster than of the diketal of aldosterone.

19-Hydroxyaldosterone is a crystalline solid, m.p. 110°–120° C., soluble in most organic solvents and *freely in water*, from which it can be recovered unchanged by evaporation in a desiccator over sulfuric acid. It adheres tenaciously to residual silica from TLC, from which it can be readily desorbed with water. Its i.r. spectrum in KBr exhibits a weak saturated carbonyl, showing that in the solid state the molecule exists mostly in the cyclic 18,20-epoxy from 12b, $^1$H-NMR spectra indicate that in $CDCl_3$ 19-hydroxyaldosterone exists mainly in two isomeric forms in the ratio 7:5, as judged by the 18-H singlets; in $D_2O$ in the ratio is 5:1.

We claim:
1. 19-Hydroxyaldosterone of the formula

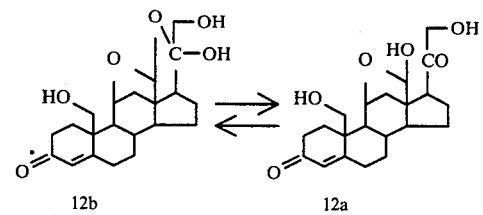

2. 19-Hydroxyaldosterone.
3. A pharmaceutical composition containing as an active ingredient 19-hydroxyaldosterone in a pharmaceutically inert carrier.
4. A method for treating Addison's disease comprising administering the pharmaceutical composition of claim 3 to a patient.
5. A process for the production of 19-hydroxyaldosterone, which comprises:
(a) acetylating 21-acetoxy-4-pregnene-3,20-dione-20-ethylene ketal-18,11β-lactone with acetic anhydride, trimethylchlorosilane and sodium iodide to produce 3,21-diacetoxy-3,5-pregnadien-20-one-20-ethylene ketal-18,11β-lactone;
(b) reducing the last mentioned compound with sodium borohydride to produce the 3β-ol 3β,21-dihydroxy-5-pregnen-20-one-20-ethylene ketal-18,11β-lactone;
(c) acetylating the 3β-ol with acetic anhydride and pyridine to produce the diacetate 3β,21-diacetoxy-5-α pregnan-20-one-20-ethylene ketal-18,11β lactone;
(d) reacting the diacetate with N-bromoacetamide and perchloric acid to produce the bromohydrin 3β, 21-diacetoxy-5-bromo-6β-hydroxy-5α-pregnane-20-one-20-ethylene ketal lactone;
(e) reacting the bromohydrin with lead tetraacetate; iodine and calcium carbonate to produce the diacetate 3β,21-diacetoxy-5-bromo-6β,19-epoxy-5α-pregnan-20-one-20-ethylene ketal-18,11β-lactone;
(f) saponifying the last mentioned diacetate with boiling bicarbonate to produce the diol 5-bromo-6β,19-epoxy-3β,21-hydroxy-5α-pregnan-20-one-20-ethylene ketal-18,11β-lactone;
(g) selectively oxidizing the diol with Jones reagent to produce the bromoketone 5-bromo-6β,19-epoxy-21-hydroxy-5-pregnane-3,20-dione-20-ethylene ketal-18,11β-lactone; P1 (h) dehydrobrominating the bromoketone with sodium acetate to produce the unsaturated ketone 6β,19-epoxy-21-hydroxy-4-pregnene-3,20-dione-20-ethylene ketal-18,11β-lactone;
(i) subjecting the unsaturated ketone to reductive ring opening with zinc in acetic acid and isopropanol to produce 19,21-dihydroxy-4-pregnen-3,20-dione-20-ethylene ketal-18, 11β-lactone and it's 5-ene isomer;
(j) ketalizing the mixture with ethylene glycol and p-toluenesulfonic acid to produce the diketal 19,21-dihydroxy-5-pregnene-3,20-dione-3,20-di-(ethylene ketal)-18,11β-lactone;
(k) reducing the diketal with diisobutyl aluminum hydride to the hemiacetal 11β,18 -epoxy-18,19,21-trihydroxy-5-pregnene 3,20-di-(ethylene ketal); and
(l) hydrolyzing the hemiacetal with acid to produce 19-hydroxyaldosterone.

* * * * *